United States Patent [19]

Weinberg et al.

[11] Patent Number: 5,476,485
[45] Date of Patent: Dec. 19, 1995

[54] AUTOMATIC IMPLANTABLE PULSE GENERATOR

[75] Inventors: Lisa P. Weinberg, Moorpark; Samuel M. Katz, Los Angeles, both of Calif.

[73] Assignee: Pacesetter, Inc., Sylmar, Calif.

[21] Appl. No.: 124,902

[22] Filed: Sep. 21, 1993

[51] Int. Cl.$^6$ ............................................. A61N 1/37
[52] U.S. Cl. ............................................. 607/28; 607/62
[58] Field of Search ............................ 607/27, 28, 29, 607/35, 37, 62

[56] References Cited

U.S. PATENT DOCUMENTS

| | | |
|---|---|---|
| 3,842,843 | 10/1974 | Mourot et al. ............................ 607/35 |
| 4,390,022 | 6/1983 | Calfee et al. . |
| 4,404,972 | 9/1983 | Gordon et al. . |
| 4,490,053 | 12/1984 | Mann et al. . |
| 4,708,144 | 11/1987 | Hamilton et al. . |
| 4,766,902 | 8/1988 | Schroeppel . |
| 4,768,511 | 9/1988 | DeCote, Jr. . |
| 4,940,052 | 7/1990 | Mann et al. . |
| 5,003,975 | 4/1991 | Hafelfinger et al. . |
| 5,040,534 | 8/1991 | Mann et al. . |
| 5,050,599 | 9/1991 | Hoegnelid . |
| 5,074,302 | 12/1991 | Poore et al. . |
| 5,314,502 | 5/1994 | McNichols et al. ...................... 607/62 |
| 5,350,407 | 9/1994 | McClure et al. ......................... 607/16 |
| 5,370,666 | 12/1994 | Lindberg et al. ........................ 607/16 |

Primary Examiner—William E. Kamm
Assistant Examiner—Scott M. Getzow
Attorney, Agent, or Firm—Lisa P. Weinberg

[57] ABSTRACT

The present invention is directed toward a pulse generator for detecting that a pulse generator and an implantable lead are properly implanted so that a plurality of automatic features can be automatically turned ON. The automatic features include: automatic sensitivity adjustment; automatic capture adjustment; automatic rate adjustment, and the automatic adjustment of associated rate-responsive parameters; automatic electrode configuration; and the automatic adjustment of other timing parameters. An impedance detector is used to detect that the electrodes are in contact with the body by determining if the lead impedance is within a prescribed range. Redundant sensors, such as a temperature sensor, a shorting plug, or a resistive load could be used to confirm that the electrodes are in contact with the body.

51 Claims, 5 Drawing Sheets

AUTOMATIC IMPLANTABLE PULSE GENERATOR

FIELD OF THE INVENTION

The present invention relates in general to implantable medical devices, and more specifically, to implantable cardiac stimulation devices which can automatically wake up when implanted and, once activated, automatically determine various parameters normally determined by the physician at implant, e.g., modes, capture and sensing thresholds.

BACKGROUND OF THE INVENTION

The technology of cardiac stimulation devices has developed into a high level of sophistication with respect to system performance. The current generation of cardiac pulse generators, or pacemakers, incorporate microprocessors and related circuitry to sense and stimulate heart activity under a variety of physiological conditions. Cardiac pulse generators may also be of the type which include arrhythmia detection and may be programmed to control the heart in correcting or compensating for various heart abnormalities, e.g., antitachycardia pacemakers, cardioverters and defibrillators. A background description of modern cardiac pacemaker technology is set forth in U.S. Pat. No. 4,712,555, which patent is incorporated herein by reference.

As the complexity of cardiac pulse generators increases, the physician is faced with numerous programmable parameters to set and measurements to take at implant. It is because of this complexity that many physicians implant the pulse generators without ever reprogramming them. As a result, the manufacturer becomes the "implanting physician" by selecting "as shipped" values that are also considered safe for implanting. For example, a single-chamber VVI pulse generator is typically shipped by the manufacturer at a rate of 70 ppm, a ventricular output of 4 volts and 0.6 ms, and a ventricular sensitivity of 2 mV. If the pulse generator is shipped in the dual-chamber mode, the pulse generator will additionally include an atrial output of 4 volts and 0.6 ms, and an atrial sensitivity of 1 mV. Some manufacturers have elected to ship their dual-chamber DDD pacemakers in a VVI mode. If the physician never reprograms the latter devices to DDD mode or changes the output amplitude to conserve current drain, both the patient's health and the performance of the pulse generator are compromised.

Automatic features have been taught in several patents and incorporated into several manufacturer's devices. For example, "automatic output regulation" or "automatic capture detection" techniques typically include: automatically adjusting the energy of the applied pacing pulses according to a prearranged routine until capture is obtained; periodically testing the threshold (particularly during the acute phase); and verifying capture on a beat-by-beat basis, providing high amplitude backup pulses when capture is lost. See, for example, U.S. Pat. No. 4,729,376 (Decote, Jr.); U.S. Pat. No. 4,708,142 (Decote, Jr.); U.S. Pat. No. 4,686,988 (Sholder); and U.S. Pat. No. 4,969,467 (Callaghan et al.).

Autosensitivity features are also well known. For example, in U.S. Pat. No. 4,768,511 (Decote Jr.), the thresholds of the two voltage comparators are automatically adjusted so that one of the voltage comparators will sense the cardiac activity of the selected heart chamber and the other voltage comparator will not sense the cardiac activity. A similar arrangement is taught in U.S. Pat. No. 4,766,902 (Schroeppel). In U.S. Pat. No. 5,050,599 (Hoegnelid) two detectors are also used with a setting means which sets the sensitivity of the first detector such that the first detector means detects every event detected by the second detector, however, the second detector senses impedance which corresponds to an electrical cardiac signal while the first detector detects electrical cardiac signals. In U.S. Pat. No. 4,708,144 (Hamilton et al.), sensitivity is automatically controlled by measuring the peak value of each R-wave, and deriving a long-term average value. The gain of the sense channel is then adjusted according to the average of the measured peak values.

In U.S. Pat. No. 5,003,975 (Duncan et al.), an "Automatic Electrode Configuration Of An Implantable Pacemaker" is shown in which lead impedance is automatically measured to determine a functioning electrode configuration (unipolar, bipolar or unipolar from the ring). If a proper impedance measurement is not sensed for the programmed configuration, additional impedance measurements for other possible configurations are made in an ordered sequence in order to determine if an improper lead has been implanted or if an electrode has broken. When an operable configuration is found, the pacemaker continues operation in that configuration, thereby ensuring that capture can continue to occur until such time as the problem which has been detected can be corrected.

Another "automatic" feature is the "rate adaptive" or "rate-responsive" mode found in some pulse generators. Once this mode is enabled the pulse generator will automatically adjust the rate according to the patient's physiological needs, e.g., emotional and/or exercise demand.

A disadvantage of all of these "automatic" features is that they must be turned ON after implanting the device. They cannot be included in the "as shipped values" because in each case the device would be endlessly searching for a desired result or disable themselves. For example, a pulse generator in an autocapture mode would endlessly search for capture and/or perform a threshold search and/or disable itself when none was found. Likewise, the autosensitivity mode would endlessly look for cardiac signals that it could calibrate to. The automatic electrode configuration mode would never find an impedance to determine the "best" electrode to program to. The rate adaptive mode would be adjusting the rate according to the selected sensor (e.g., motion, temperature, etc.). Shelf-life is significantly affected by the dynamic current drain caused by the microprocessor constantly waking up to perform unnecessary pacemaker operations. Thus, it should be apparent that the current drain would be too excessive to permit shipping in these "automatic" modes.

What is needed is a pulse generator which will automatically turn itself ON at implant and automatically set itself to operate at safe thresholds for the patient, to initiate other "automatic" features," while still conserving power consumption, particularly during the "shelf-life" of the pulse generator. The present invention addresses these and other needs.

SUMMARY OF THE INVENTION

The present invention is directed toward a system for detecting that a pulse generator and an implantable lead are properly implanted so that a plurality of automatic features can be automatically turned ON. Thus, the present invention is directed towards a "fully automatic" and "intelligent" pulse generator.

In the preferred embodiment, an impedance detector is used to detect that the electrodes are in contact with the body by determining if the lead impedance is within a prescribed range, for example, between 100 to 2000 ohms. The preferred embodiment also employs redundant methods of detecting that a pulse generator and an implantable lead are implanted. For example, a temperature sensor may be used to quickly detect body temperature and confirm that the lead and/or pulse generator has been implanted. As an alternative redundant sensor or as a second confirming sensor, a shorting plug (or a resistive load) could be inserted into the output channel of a pulse generator. An impedance measurement by the impedance detector can be used to detect the presence or removal of the shorting plug.

In the preferred embodiment, at least two sensors are used to reliably detect that the pulse generator has been properly connected to an implanted lead. The precise two sensors employed would depend to a large extent on the features currently in a manufacturer's product. For example, temperature sensors are well known in the art for rate-responsive purposes. Such a device may select the combination of lead impedance and temperature to detect that the lead/pulse generator has been implanted. Other manufacturers may already be shipping their devices with a resistive load (so that they may verify that the lead impedance feature is functional after sterilization). These latter devices may opt to detect the resistive load, followed by a proper tissue-electrode lead impedance.

Thus, the advantages of the present system include: saving current consumption during the pulse generator's shelf life (thereby prolonging battery life); and providing a pulse generator which can automatically determine appropriate operating parameters, both at implant and during the life of the pulse generator. In theory, the system would not need a programmer system and could simply be verified for proper functionality by using an ECG recorder. In the extreme case, where the physician does not have a programmer or an ECG recorder, the present invention could alert the physician of a malfunction by sounding an audible alarm.

BRIEF DESCRIPTION OF THE INVENTION

Further features and advantages of the present invention may be more readily understood by reference to the following description taken in conjunction with the accompanying drawings, in which:

FIG. 5 is a flow chart describing the preferred embodiment of the step of "programming the automatic features ON," shown in FIG. 2, which includes, but is not limited to, programming automatic sensitivity, automatic capture, rate response, and automatic electrode configuration modes ON;

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
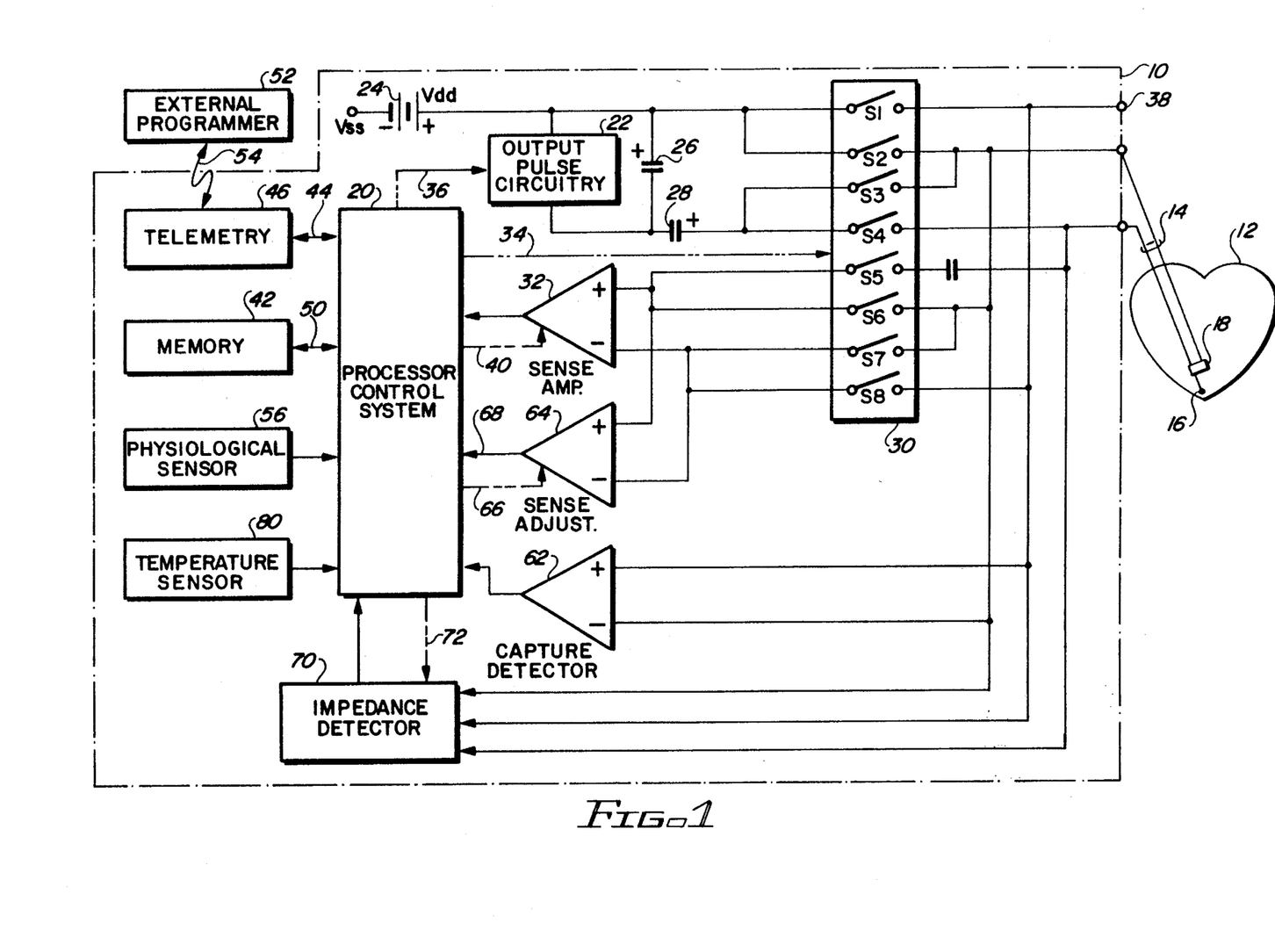
FIG. 1 is a functional block diagram of a single-chamber embodiment of an automatic implantable pulse generator, illustrating the basic elements of an automatic implantable pulse generator.

In FIG. 1, a simplified block diagram of a single-chamber embodiment of an automatic implantable pulse generator is shown. A single-chamber pulse generator 10 is illustrated coupled to a heart 12 by way of a lead 14. The lead 14 is shown as a bipolar lead (i.e., having a tip electrode 16 and a ring electrode 18) because of the many benefits of bipolar leads. For example, capture detection, which is one of the desired automatic features of the preferred embodiment, is superior when used with bipolar electrodes. Also, it is well known that bipolar stimulation can eliminate pectoral stimulation; bipolar sensing can eliminate sensing of noise and EMI; and further, if a wire fractures, automatic electrode configuration (described in more detail below) can reprogram the electrode configuration to an alternative pair of operable electrodes. While a single-chamber, bipolar system is shown, this is only to illustrate the basic functional blocks. It is understood that one skilled in the art could adapt the present invention to be used in either a dual-chamber device or with unipolar leads.

Controlling the single-chamber pulse generator 10 is a processor control system 20. As is well known in the art, the processor control system 20 could be constructed from dedicated logic and timing circuitry, state machine circuitry, or a microprocessor.

Output pulse circuitry 22 generates stimulation pulses to the tip electrode 16 through the lead 14. The output pulse circuitry 22 is coupled to a battery 24 which charges a capacitor 26 to a desired or programmed value. When the capacitor 26 is fully charged, the charge is delivered to the heart 12 through an output capacitor 28. The ventricular output pulse is referred to as the "V-pulse." The processor control system 20 generates trigger signals to the output pulse circuitry 22 over signal line 36 to control both the rate and the inhibition of the stimulation pulses. A switch bank 30 (described in more detail below) determines the polarity of the stimulation pulses, e.g., unipolar or bipolar, by selectively closing the appropriate switches.

A sense amplifier 32 is coupled to the lead 14 through the switch bank 30 and detects the presence of cardiac activity. The sense amplifier 32 is connected to the processor control system 20 which will inhibit the output pulse circuitry 22 whenever cardiac activity is sensed, in a demand fashion. The sense amplifier 32 receives control signals over signal line 40 from the processor control system 20. These control signals include controlling the gain (sensitivity) and the timing of any blocking circuitry (not shown) coupled to the inputs of the sense amplifier 32. The switch bank 30 likewise controls the polarity of the sense amplifier 32 in one of three sensing configurations, i.e., tip-ring, tip-case or ring-case.

The switch bank 30 receives a control signal 34 from the processor control system 20 which enables the appropriate combination of switches, S1–S8, to turn ON or OFF. Switches S1 and S2 connect either a case electrode 38 or the ring electrode 18, respectively, to the positive terminal of capacitor 26, thus enabling either the case 38 or ring electrode 18 to act as the return electrode for the output pulse circuitry 22. Switch S4 connects the tip electrode 16 to the negative terminal of the capacitor 26, thus acting as the cathode or stimulating electrode. Alternatively, Switch S3 could be used to connect the ring electrode as the stimulating electrode (typically, the ring is used for stimulation only if the tip electrode is defective). In this way, the physician may program the stimulation pulses (via an external programmer 52) to be either tip-ring, tip-case or ring-case. For example, the processor control system 20 would close switches S4 and S2 for tip-ring pacing; switches S4 and S1 for tip-case pacing; and switches S3 and S1 for ring-case pacing.

The physician may also program the polarity of the sense amplifiers, independent of the stimulation polarity. For example, the processor control system 20 would close switches S5 and S7 for tip-ring sensing; switches S5 and S8 for tip-case sensing; and switches S6 and S8 for ring-case sensing.

The processor control system 20 also controls the rate at which the output pulse circuitry 22 generates stimulation pulses, as well as keeping track of the timing of any refractory period, PVARP intervals, noise detection windows, alert intervals, etc., as is known in the art.

The processor control system 20 is connected to a memory circuit 42 by a suitable data/address bus 44. This memory circuit 42 allows certain control parameters, used by the processor control system 20 in controlling the operation of the pulse generator 10, to be programmably stored and modified, as required, in order to customize the operation of the pulse generator 10 to suit the needs of a particular patient. Further, data sensed during the operation of the pulse generator 10 may be stored in the memory circuit 42 for later retrieval and analysis.

A telemetry circuit 46 is further included in the pulse generator 10. This telemetry circuit 46 is connected to the processor control system 20 by way of a suitable command/data bus 50. In turn, the telemetry circuit 46 may be selectively coupled to an external programming device 52 by means of an appropriate communication link 54, which may be any suitable electromagnetic link, such as an RF (radio frequency) link. Advantageously, through the external programmer 52 and the communication link 54, desired commands may be sent to the processor control system 20 and data (either held within the processor control system 20, as in a data latch, or stored within the memory circuit 42,) may be remotely received from the pulse generator 10. In this manner, noninvasive communications may be established with the implanted pulse generator 10 from a remote, non-implanted location.

In the preferred embodiment, the pulse generator 10 includes a physiologic sensor 56. While the physiologic sensor 56 is illustrated in FIG. 1 as being included within the pulse generator 10, it is to be understood that the physiologic sensor 56 may also be external to the pulse generator 10, yet still be implanted within or carried by the patient. The physiological sensor 56 is used to detect the exercise state of the patient, to which the processor control system 20 responds by adjusting the rate at which the output pulse circuitry 22 generates stimulation pulses. Such sensors are commonly called "rate-responsive" sensors. A common type of rate-responsive sensor is an activity sensor, such as a piezoelectric crystal, which is mounted to the can or case of the pulse generator 10. Other types of physiologic sensors are also known, such as sensors which sense the oxygen content of blood, respiration rate, pH of blood, body motion, and the like. The type of sensor used is not critical to the present invention. Any sensor which is capable of sensing some physiological parameter which is relatable to the rate at which the heart should be beating may be used.

In the preferred embodiment, the present invention employs automatic capture detection. As illustrated in FIG. 1, this may be performed by a capture detector 62. The capture detector 62 detects a depolarization signal during a window following a stimulation pulse, the presence of which indicates capture has occurred. It is also known in the art to use the sense amplifier 32 to perform this function. Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold. The value of the safety margin would depend on whether capture detection is to be performed on a beat-by-beat basis or only sampled. For example, capture detection performed on a beat-by-beat basis could have a safety margin just slightly above threshold, whereas capture every 4 or 8 beats would require a slightly larger safety margin to ensure that capture is not lost in between verification times.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); and U.S. Pat. No. 4,969,467 (Callaghan et al.), which patents are hereby incorporated herein by reference. The type of capture detection system used is not critical to the present invention. Any system which is capable of detecting capture may be used.

The present invention further employs automatic sensitivity adjustment circuitry 64. In FIG. 1, it is depicted as an amplifier coupled to corresponding inputs of the sense amplifier 32. The automatic sensitivity adjustment circuitry 64 receives control signals over signal line 66 from the processor control system 20 and has an output 68 which is coupled to the processor control system 20. Based on the output of the automatic sensitivity adjustment circuitry 64, the processor control system 20 can adjust the sensitivity of the sense amplifier 32. The type of automatic sensitivity adjustment system used is not critical to the present invention. Any system which is capable of automatically adjusting the sensitivity may be used. For example, the automatic sensitivity adjustment circuitry 64 could comprise a second sense amplifier having a slightly lower sensitivity threshold than the sense amplifier 32. Under control of the processor control system 20, the sensitivities of both amplifiers may be adjusted until one amplifier senses when the other does not. For a complete description of this method, see either U.S. Pat. No. 4,768,511 (Decote, Jr.) or U.S. Pat. No. 4,766,902 (Schroeppel), both of which are incorporated herein by reference. Alternatively, the automatic sensitivity adjustment circuitry 64 could employ a peak detector as describe in U.S. Pat. No. 4,708,144 (Hamilton et al.), which is also incorporated herein by reference.

The present invention also preferably employs a system for automatically configuring the electrode polarity to an operable pair of electrodes. As shown in FIG. 1, an impedance detector 70 is directly coupled to the lead 14 and to the case electrode 38. The processor control system 20 provides control signals over signal line 72 to direct the impedance detector 70 which pair of electrodes to take a measurement between. This technique is well known in the art for detecting lead failures. By detecting an impedance between an electrode pair, the processor control system 20 can determine an operable electrode configuration and adjust the switch bank 30 to deliver stimulation pulses and sense cardiac signals between the operable pair of electrodes. A more detailed discussion of automatic electrode configuration can be found in U.S. Pat. No. 5,003,975 (Duncan et al.), which reference is incorporated herein by reference.

The present invention is directed toward a system for detecting that a pulse generator and an implantable lead are implanted so that all of the automatic features can be automatically turned ON. Without this invention, automatic features must be shipped in their OFF state and programmed ON by the physician, otherwise they would be endlessly stuck searching for capture thresholds, sensitivity signals, measurements, rate thresholds, etc.

The preferred embodiment further employs redundant methods of detecting that a pulse generator and an implantable lead are implanted. In the present invention, the impedance detector 70, coupled with the processor control system 20, is used to detect that the lead 14 is in contact with the body by determining if the lead impedance is within a prescribed range. When the measured impedance is within, for example, 100 to 2000 ohms, then the processor control system 20 assumes that a lead has been implanted and properly connected to the pulse generator 10.

A temperature sensor 80 is used as a redundant method of detecting that the pulse generator 10 and/or the lead (depending on the location of the temperature sensor 80) has been implanted. For example, a thermistor located inside the pulse generator or on the lead could quickly detect body temperature and confirm that the lead and/or pulse generator has been implanted.

As an alternative redundant sensor or as a second confirming sensor, a shorting plug (not shown) could be inserted into the output channel of a pulse generator's connector top (not shown), i.e., across the tip and ring terminals. An impedance measurement by the impedance detector 70 can be used to detect the presence of the shorting plug. When the physician removes the shorting plug at implant, the impedance detector 70 will detect the absence of the shorting plug (i.e., an open circuit) until such time that the pulse generator 10 is connected to an implanted lead. If it is desired to ship the pulse generator 10 with a resistive load (for purposes of testing the functionality of the device after sterilization), the impedance detector 70 will assume that the pulse generator has not been implanted if it consistently detects a precisely known value of a resistive load.

Significant routines are hereinafter discussed with reference to operational flow diagrams. It will be appreciated that these flow diagrams can be implemented by a variety of specific process instructions prepared by persons skilled in the programming art and the present invention resides in the process and not the implementation.

Figure 2:
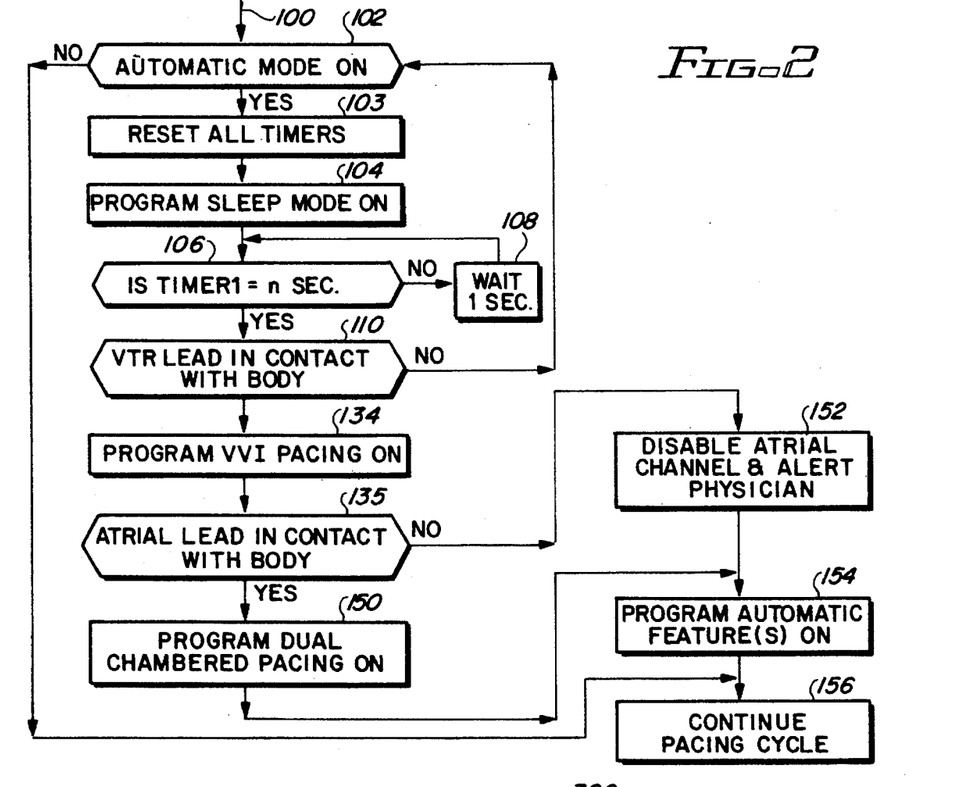
FIG. 2 is a flow chart describing an overview of the operation of the preferred embodiment, a dual-chamber, automatic implantable pulse generator, configured in accordance with the teachings of the present invention.

In FIG. 2, a flow chart describing an overview of the operation of the automatic implantable pulse generator of the present invention is shown. In this flow chart, and the other flow charts described herein, the various steps are summarized in individual "blocks" or boxes. Such blocks describe specific actions or decisions that must be made or carried out as the algorithm proceeds. Specific circuitry that carries out these steps can readily be fashioned by those skilled in the art. Particularly, where a microprocessor or equivalent programmable control device is employed as a key element of the pulse generator, the flow charts presented herein provide the basis for a "control program" that may be used by such microprocessor, or equivalent, to effectuate the desired control of the pulse generator. Those skilled in the arts may readily write such a control program based on the flow charts and other descriptions presented herein.

As shown in FIG. 2, the flow chart begins with an arrow 100. This arrow 100 schematically represents that the flow chart of FIG. 2 forms a portion of an overall control program associated with the process control system 20. In the preferred embodiment, shown in FIGS. 2–6, the pulse generator is a bipolar, dual-chamber device. One of ordinary skill in the art could easily adapt the single-chamber pulse generator shown in FIG. 1 to include a second channel coupled to a lead in the atrium by simply duplicating the associated components shown for the ventricular lead. One skilled in the art could also easily adapt the flow charts shown in FIGS. 2–6 to use only a single-chamber device.

In the preferred embodiment shown in FIG. 2, the pulse generator may be programmed by the manufacturer to be automatic or manual. Thus, a test is performed, at block 102, to detect if the automatic mode has been programmed ON. If it is OFF, then the present invention is bypassed and pulse generator returns to normal pacing functions (block 156). If the automatic mode is programmed ON, then all of the timers are reset (block 103) and the pulse generator goes into a sleep, or storage, mode (block 104) in which high current drain functions are disabled, e.g., turning OFF the output pulse circuitry 22, the sense amplifier(s) 32, and reducing the duty cycle of the processor control means 20.

At block 106, a determination is made as to whether or not it is time to test if the lead is in contact with the body (block 110). That is, timer (Timer1) is checked to see if a desired interval, "n" seconds, has elapse. If it has not, then the system waits 1 second (block 108) and retests. The time interval is chosen based on a compromise between the amount of current drain savings required and the amount of delay a physician would see before the device would turn ON. If Timer1 has timed out (block 106), then the test is performed to determine if the ventricular lead is in contact with the body (block 110). The test (block 110) is shown in more detail in FIG. 3.

Figure 3:
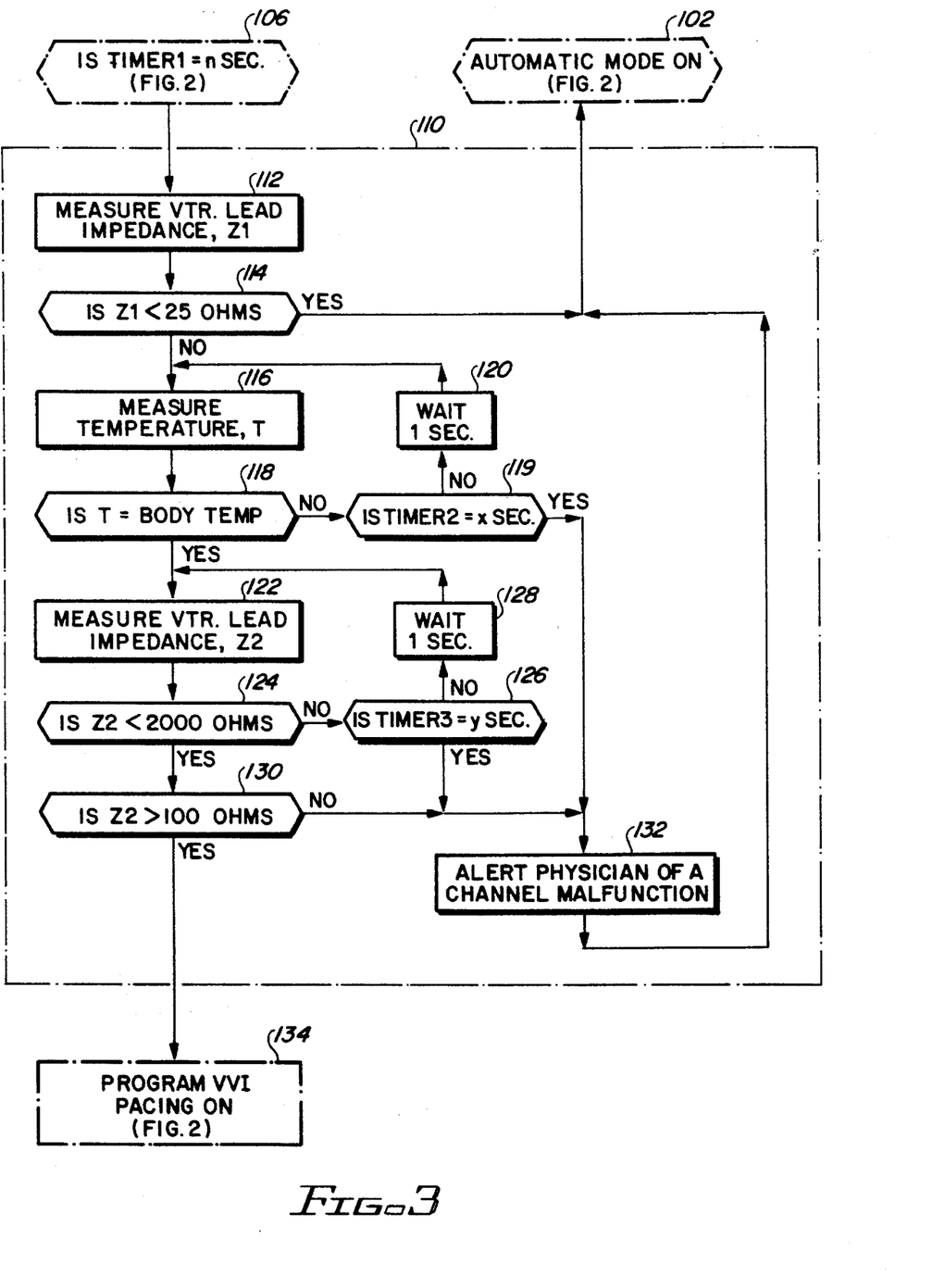
FIG. 3 is a detailed flow chart describing the step of "detecting a ventricular lead in contact with body tissue," shown in FIG. 2.

In the preferred embodiment shown in FIG. 3, all three methods of detecting if the pulse generator has been implanted are included: using the shorting plug; using the temperature sensor 80; and using the impedance detector 70. Although it is recognized that any single method could be used, it is preferred to have at least a combination of two sensors.

As shown in FIG. 3, the first step is to detect the absence or presence of the shorting plug. A ventricular lead impedance, Z1, is measured (block 112) across the ventricular tip and ring electrode using the impedance detector 70 (shown in FIG. 1). If a ventricular shorting plug has not been removed (indicating that the pulse generator is still in its sterile package), then the lead impedance will be essentially zero (block 114). Thus, the program will return to the beginning of the routine (block 102, FIGS. 2 and 3) and go back to the sleep mode until the next wakeup. If, on the other hand, the ventricular shorting plug has been removed, then the lead impedance will be greater than 25 ohms (actually, it will be an open circuit until such time that the lead is implanted and connected to the pulse generator).

The successful detection of the removal of the shorting plug (at block 114) will initiate a temperature measurement (block 116) and a determination of whether the temperature is body temperature (test 118), thus confirming that the device has been implanted.

If the temperature sensor is not at body temperature, then the system will either repeat the measurement after a short delay or exit the program after "x" seconds have elapsed, thereby indicating a malfunction. The time interval, x, is selected to allow the physician sufficient time to implant the lead/pulse generator, while still indicating a problem if the proper temperature is not found within a reasonable time. This is achieved using a second timer, Timer2, to determine if "x" seconds have elapsed (block 119). If Timer2 is less than "x" seconds, the pulse generator will wait 1 second (block 120) and then repeat the measurement (block 116). If Timer2 is greater than "x" seconds, then the physician will be alerted (block 132) of a malfunction, either by sounding an audible alarm (not shown) or by telemetry back to the external programmer.

After a body temperature is successfully detected (block 118), a ventricular lead impedance, Z2, is measured (block 122) across the ventricular tip and ring electrode. If the lead impedance, Z2, is still greater than 2000 ohms (block 124), one of two things could be happening: (1) the lead has not yet been connected to the pulse generator or (2) the lead has a broken conductor.

If the lead impedance is not less than 2000 ohms, then the system will either repeat the measurement after a short delay or exit the program after "y" seconds have elapsed, thereby indicating a malfunction. The time interval, y, is selected to allow the physician sufficient time to connect the lead to the pulse generator, while still indicating a problem if the proper lead impedance is not found within a reasonable time. This is achieved using a third timer, Timer3, to determine if "y" seconds have elapsed (block 126). If Timer3 is less than "y" seconds, the pulse generator will wait 1 second (block 128) and then repeat the measurement (block 122). If Timer3 is greater than "y" seconds, indicating that there may be a conductor failure, then the physician will be alerted (block 132) of a malfunction, either by sounding an audible alarm (not shown) or by telemetry back to the external programmer. Thus, the program will return to the beginning of the routine (block 102, FIGS. 2 and 3) and go back to the sleep mode until the next wakeup. If, on the other hand, the lead impedance, Z2, is less than 2000 ohms (indicating that the lead has been connected to the pulse generator), then a determination is made (block 130) to ensure that the lead is not shorted or abnormally low.

Typically, the range for normal lead impedances for a "good" lead may vary between 250 and 900 ohms, depending on the electrode size, materials, and polarity selected (unipolar or bipolar). The criteria of 100 to 2000 ohms has been chosen to encompass even poor leads which are still in patients and were designed with older technology. If the lead impedance, Z2, is within the range of 100 to 2000 ohms, and if the temperature is at body temperature and the ventricular shorting plug is removed, then there is a high degree of confidence that the lead and pulse generator are implanted, i.e., the pulse generator has been removed from its sterile package and prepared for implantation, physically placed in the body, and properly connected to a lead which is in good electrical contact with body tissue. Thus, the pulse generator will program single-chamber VVI pacing ON (block 134, FIGS. 2, 3 and 4).

Given that the preferred embodiment is a dual-chamber pulse generator, a test is performed to determine if an atrial lead has been implanted (block 135, FIG. 2). As is shown in more complete detail in FIG. 4, an atrial lead impedance, Z3, is measured (block 136) across an atrial tip and ring electrode using the lead impedance detector 70 (shown in FIG. 1).

If the atrial shorting plug has not been removed (indicating that the atrial lead has not yet been connected), then the lead impedance detected will be essentially zero (block 137). Thereafter, the system will either repeat the measurement after a short delay or exit the program after "p" minutes have elapsed, thereby indicating a malfunction. The time interval, p, is selected to allow the physician sufficient time to connect the atrial lead to the pulse generator, while still indicating a problem if the proper lead impedance is not found within a reasonable time. Thus, a fourth timer, Timer4, determines if "p" minutes have elapsed (block 138). If Timer4 is less than "p" minutes, the pulse generator will wait 1 second (block 140) and then repeat the measurement (block 136). If Timer4 is greater than "p" minutes, indicating that there may be a conductor failure or the plug has not been removed, then the physician will be alerted (block 152, FIGS. 2 and 4) of a malfunction (either by sounding an audible alarm or via telemetry) and the atrial channel would be disabled. If, on the other hand, the shorting plug has been removed, then the lead impedance will be greater than 25 ohms at block 137 (actually, it will be an open circuit until such time that the atrial lead is implanted and connected to the pulse generator).

Figure 4:
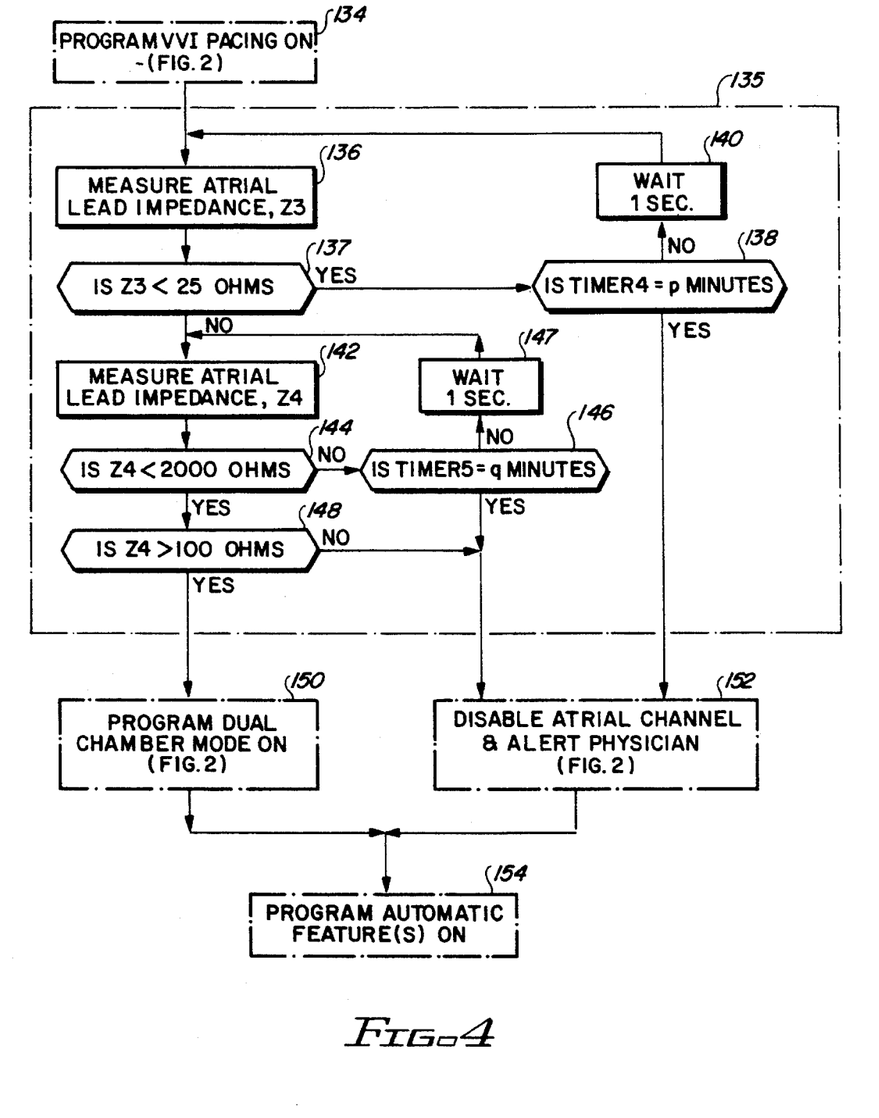
FIG. 4 is a detailed flow chart describing the step of "detecting an atrial lead in contact with body tissue," shown in FIG. 2.

Thereafter, an atrial lead impedance, Z4, is measured (block 142) across the atrial tip and ring electrode. If the atrial lead impedance, Z4, is still greater than 2000 ohms (block 144), one of two things could be happening: (1) the atrial lead has not yet been connected to the pulse generator or (2) the atrial lead has a broken conductor.

The system will repeat the measurement until "q" minutes have elapsed, after which time the system will exit and alert the physician of a malfunction. That is, a fifth timer, Timer5, determines if "q" minutes have elapsed (block 146). If Timer5 is less than "q" minutes, the pulse generator will wait 1 second (block 147) and then repeat the measurement (block 142). If Timer5 is greater than "q" minutes, indicating that there may be a conductor failure, then the physician will be alerted (block 152, FIGS. 2 and 4) of a malfunction and the atrial channel would be disabled (i.e., only single-chamber VVI pacing will be enabled).

If, on the other hand, the atrial lead impedance, Z4, is less than 2000 ohms (indicating that the lead has been properly connected to the pulse generator), then a determination is made (block 148) to ensure that the lead is not shorted or abnormally low. If the lead impedance, Z4, is within the range of 100 to 2000 ohms, the pulse generator will program dual-chamber pacing mode ON (block 150, FIGS. 2 and 4).

The automatic features would then be programmed ON (block 154, FIGS. 2, 4 and 5) for only the operative lead(s), i.e., the lead(s) having an impedance in the expected range of impedances.

Figure 5:
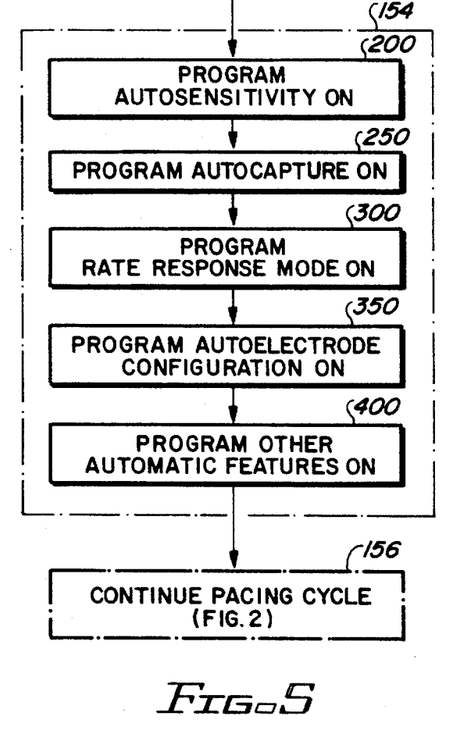

In FIG. 5, the preferred sequence of programming automatic features ON (block 154, FIG. 2) is shown. In the preferred embodiment, autosensitivity features would be enabled first (block 200), followed by autocapture (block 250), rate-response mode (block 300), autoelectrode configuration (block 350), and any other programmable features (block 400).

Figure 6:
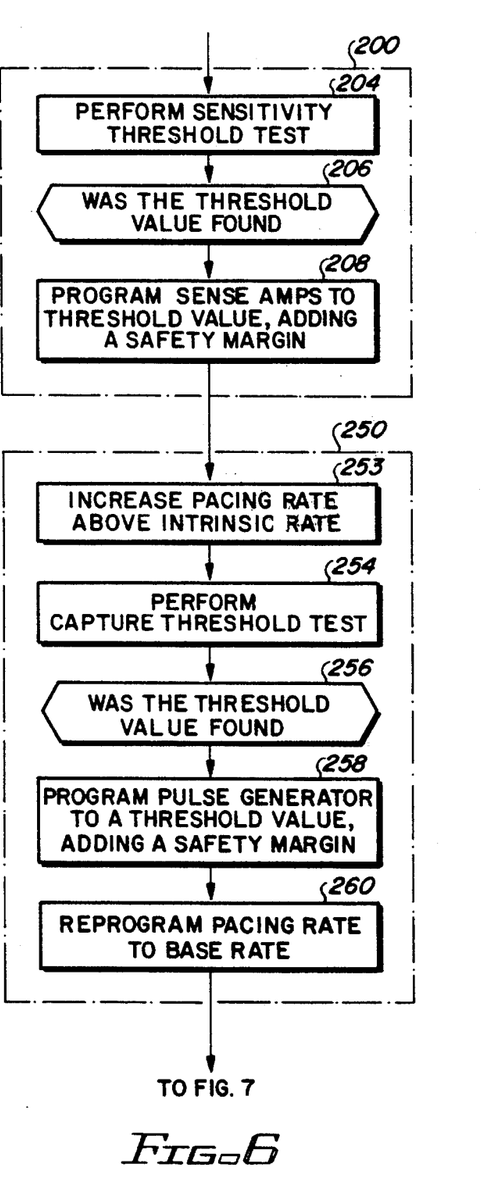
FIG. 6 is a flow chart describing the operation of the preferred sequence of steps for the automatic sensitivity and automatic capture modes shown in FIG. 5.

As shown the detailed flow chart in FIG. 6, the step of programming autosensitivity mode ON (block 200, FIG. 5) would consist of initiating a sensitivity threshold test (block 204), determining if a threshold value was found (block 206), and automatically programming the sense amplifier 32 to one of a plurality of sensitivities based on the threshold value plus a safety margin (block 208). This process would be repeated for each channel (not shown).

As further shown in the detailed flow chart in FIG. 6, the step of programming autocapture mode ON (block 250, FIG. 5) would consist of increasing the pacing rate above the intrinsic rate (block 253), initiating a capture threshold test (block 254), determining if a threshold value was found (block 256), automatically programming the pulse generator to one of a plurality of energy levels based on the threshold value plus a safety margin (block 258), and reprogramming the pacing rate back to the Base Rate (block 260). This process would also be repeated for each channel (also not shown).

Figure 7:
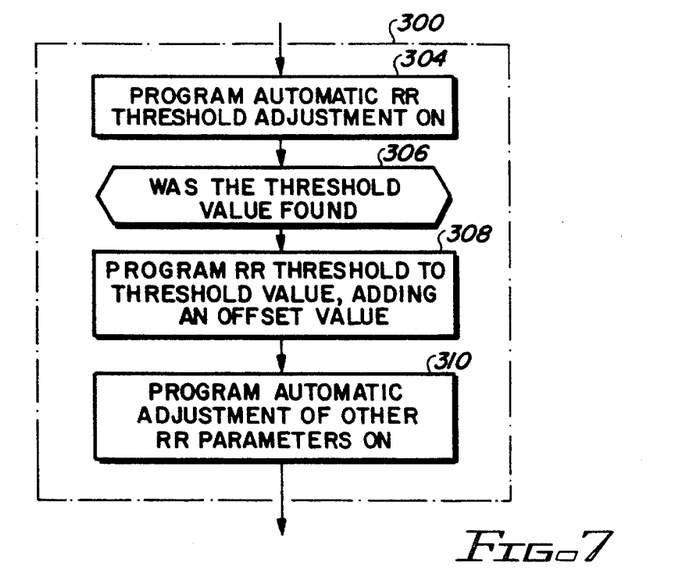
FIG. 7 is a flow chart describing the operation of the rate-response mode with the automatic adjustment of rate-response parameters.

As shown in FIG. 7, the step of programming the automatic adjustment of rate (i.e., rate-response mode) ON (block 300, FIG. 5) would consist of initiating a rate-response threshold test (block 304), determining if a threshold value was found (block 306), programming the pulse generator to a value corresponding to the threshold value plus an offset value (block 308), and programming other automatically adjustable rate-responsive parameters (block 310). For examples of automatically adjustable rate-responsive parameters, see U.S. Pat. Nos. 4,940,053 (Mann et. al); 4,940,052 (Mann et. al); and 5,024,222 (Thacker); and U.S. patent application Ser. Nos. 07/844,818 and 07/844,807, all of which are assigned to the same assignee as the present invention and are hereby incorporated herein by reference.

At block 350 (FIG. 5), the automatic electrode configuration routine (described above and already incorporated by reference) could be programmed ON to ensure the long term reliability of the pacing system. At block 400, any other automatic feature, such as automatic A-V delay adjustment, automatic blanking window adjustment, automatic refractory period adjustment, etc. could be invoked. These automatic features are well known in the art.

It will therefore be perceived that the advantages of the present invention result in a fully automatic implantable pulse generator which can adapt itself to the prevailing needs of the patient, can considerably simplify the programming of the device at implant, while providing the maximum current drain savings during its shelf life. Thus, the present invention provides a higher quality of life for the patient, making the method of the present invention a highly desirable enhancement to implantable cardiac pulse generator therapy.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An automatic implantable pulse generator, the pulse generator having a pair of output terminals, comprising:

pulse generating means for generating stimulation pulses to a patient's heart through the pair of output terminals;

a biocompatible housing for housing the pulse generating means;

means for detecting when the housing has been implanted, the detecting means including means for measuring an impedance between the pair of output terminals, the detecting means further including means for determining when the impedance is within a predetermined range of impedances corresponding to normal cardiac tissue;

means for operating the pulse generating means in a storage mode when the detecting means detects that the housing has not been implanted; and means for operating the pulse generating means in at least one automatic mode when the detecting means detects that the housing has been implanted.

2. The pulse generator recited in claim 1, wherein the range of impedances corresponding to normal cardiac tissue comprises 100–2000 ohms.

3. The pulse generator recited in claim 1, wherein the pulse generator is stored in a sterile package, the detecting means further comprises:

a redundant detecting means for verifying that the housing has been implanted.

4. The pulse generator recited in claim 3, wherein the redundant detecting means comprises:

a load connected between the pair of output terminals prior to storing the pulse generator in the sterile package, the load having a predetermined value; and wherein the determining means determines when the impedance is outside a range of impedances corresponding to the predetermined value of the load, thereby indicating that the housing has been removed from the sterile package and a physician has removed the load in preparation for implantation.

5. The pulse generator recited in claim 4, wherein:

the load comprises a shorting plug connected between the pair of terminals; and the predetermined resistive value corresponds to a short.

6. The pulse generator recited in claim 4, wherein:

the load comprises a resistive load connected between the pair of terminals; and wherein the predetermined range corresponds to the value of the resistive load.

7. The pulse generator recited in claim 3, wherein the redundant detecting means comprises:

means for sensing temperature; and means for determining when the temperature sensing means detects a temperature within a predetermined range corresponding to body temperature, thereby indicating that the housing is in contact with the body.

8. The pulse generator recited in claim 7, wherein the sensing means comprises a thermistor located in the implanted lead.

9. The pulse generator recited in claim 7, wherein the sensing means comprises a thermistor located in the housing.

10. The pulse generator recited in claim 1, wherein the detecting means comprises at least two detecting means.

11. The pulse generator recited in claim 10, wherein the at least two detecting means are selected from the group of detecting means comprising:

means for detecting that the pulse generating means has been properly connected to an implanted lead in contact with body tissue;

means for detecting that the housing has been prepared for implantation;

means for detecting that the housing is in physical contact with the body; and means for detecting that an implantable lead is in physical contact with the body.

12. The pulse generator recited in claim 1, wherein the means for operating the pulse generating means in a storage mode comprises:

means for disabling a desired number of pacing functions; and means for periodically triggering the detecting means to detect if the pulse generating means has been properly connected to an implantable lead in contact with body tissue.

13. The pulse generator recited in claim 12, further comprising:

means for sensing cardiac signals;

wherein the disabling means comprises means for disabling the pulse generating means and the sensing means.

14. The pulse generator recited in claim 12, further comprising:

processing means for controlling a plurality of modes of operations for the pulse generating means; and wherein the disabling means comprises means for reducing the duty cycle of the processor means.

15. The pulse generator recited in claim 1, wherein:

the pulse generating means includes means for operating in a rate responsive mode, the rate responsive mode being defined by a plurality of rate responsive parameters;

the means for operating the pulse generating means in at least one automatic mode comprises means for automatically determining the plurality of rate responsive parameters so that the pulse generator may operate in the rate-responsive mode.

16. The pulse generator recited in claim 15, wherein the means for operating in the rate-responsive mode comprises:

timing means for generating stimulation pulses at a desired rate;

a physiological sensor for sensing physiological need;

means for measuring the value of the physiological sensor periodically over a predetermined period;

means for automatically determining a plurality of operating parameters based on the value of the physiological sensor measured over the predetermined period;

means for programming the plurality of operating parameters into the pulse generating means; and means for automatically adjusting at least the rate of stimulation pulses according to the sensed physiological need.

17. The pulse generator recited in claim 1, wherein the means for operating the pulse generating means in at least one automatic mode comprises means for operating in an automatic sensitivity mode.

18. The pulse generator recited in claim 17, wherein the means for operating in the automatic sensitivity mode comprises:

sensing means for sensing cardiac signals, the sensing means having a plurality of sensitivity settings;

means for periodically detecting sensitivity threshold; and means for automatically adjusting the sensing means to one of the plurality of sensitivity settings based on the detected sensitivity threshold.

19. The pulse generator recited in claim 1, wherein the means for operating the pulse generating means in at least one automatic mode comprises means for operating in an automatic capture mode.

20. The pulse generator recited in claim 19, wherein the means for operating in the automatic capture mode comprises:

means for generating stimulation pulses at a desired energy level;

means for detecting capture following a stimulation pulse generated by the generating means;

means for periodically detecting capture at the lowest energy level; and means for programming the energy level of the stimulation pulse based on the detected capture threshold.

21. The pulse generator recited in claim 1, wherein the means for operating the pulse generating means in at least one automatic mode comprises means for operating in an automatic electrode configuration mode.

22. The pulse generator recited in claim 21, wherein the pulse generating means is connected to an implantable lead having a tip, a ring, wherein the housing acts as a case electrode, wherein the means for operating in the automatic electrode configuration mode comprises:

means for detecting an operable pair of electrodes in contact with body tissue; and means for automatically programming an electrode configuration for the pulse generator to the operative pair of electrodes.

23. The pulse generator recited in claim 22, wherein the means for detecting an operable pair of electrodes in contact with body tissue comprises:

means for measuring impedance between a pair of electrodes; and means for determining when the impedance is within a predetermined range corresponding to normal cardiac tissue.

24. The pulse generator recited in claim 1, wherein the pulse generating means includes sensing means for sensing cardiac activity, and wherein the means for operating the pulse generating means in at least one automatic mode comprises:

means for programming the sensing means in an automatic sensitivity mode; and means for programming the pulse generating means in an automatic capture mode.

25. The pulse generator recited in claim 24, wherein the sensing means has a plurality of sensitivity settings, further comprising:

means for programming a sensitivity threshold test to determine the optimum sensitivity setting for the sensing means;

means for programming a capture threshold test to determine an optimum output pulse value for the pulse generator;

means for programming the sensing means to the optimum sensitivity setting; and means for programming the pulse generator to optimum output pulse value.

26. An automatic implantable pulse generator, comprising:

pulse generating means for generating stimulation pulses to a patient's heart;

a biocompatible housing for housing the pulse generating means;

means for operating the pulse generating means in a plurality of automatic modes;

means for detecting when the housing has been implanted; and means for programming the mode of operation to a low current drain mode when the detecting means detects that the housing has not been implanted, and for programming the mode of operation to at least one of the plurality of automatic modes when the detecting means detects that the housing has been implanted.

27. The pulse generator recited in claim 26, wherein the pulse generator includes a pair of output terminals, wherein the detecting means comprises:

means for measuring impedance between the pair of output terminals; and means for determining when the impedance is within a predetermined range corresponding to normal cardiac tissue.

28. The pulse generator recited in claim 27, wherein the predetermined range comprises 100–2000 ohms.

29. The pulse generator recited in claim 27, wherein the detecting means comprises a redundant detecting means.

30. The pulse generator recited in claim 29, wherein the redundant detecting means comprises:

a shorting plug connected between the pair of output terminals; and means for determining when the shorting plug has been removed.

31. The pulse generator recited in claim 29, wherein the redundant detecting means comprises:

a resistive load connected between the pair of output terminals; and means for determining when the resistive load has been removed.

32. The pulse generator recited in claim 29, wherein the redundant detecting means comprises:

means for sensing temperature; and means for determining when the temperature sensing means detects a temperature within a predetermined range corresponding to body temperature.

33. The pulse generator recited in claim 26, wherein the means for programming the mode of operation to a low current drain mode comprises:

means for disabling a desired number of pulse generator modes of operation; and means for periodically triggering the detecting means to detect if the pulse generating means has been properly connected to an implantable lead in contact with body tissue.

34. The pulse generator recited in claim 26, wherein the means for operating the pulse generator in a plurality of automatic modes comprises at least one of automatic sensitivity adjustment mode, automatic capture mode, automatic rate adjustment mode, automatic electrode configuration mode.

35. A method of automatically operating an implantable pulse generator, the implantable pulse generator having pulse generating means for generating stimulation pulses, the pulse generating means being enclosed in a biocompatible housing with a pair of output terminals therethrough, the method comprising the steps of:

measuring impedance between the pair of output terminals;

detecting when the housing has been implanted by determining when the impedance is within a predetermined range corresponding to body tissue impedance;

automatically programming the pulse generating means in a storage mode when the detecting means detects that the housing has not been implanted; and automatically programming the pulse generating means in at least one automatic mode when the detecting means detects that the housing has been implanted.

36. The method recited in claim 35, wherein the detecting step comprises the step of:

verifying that the housing has been implanted using a redundant sensor.

37. The method recited in claim 36, wherein the implantable pulse generator is stored in a sterile package, wherein the verifying step comprises the steps of:

connecting a shorting plug between the pair of output terminals prior to storing the pulse generator in the sterile package; and determining when the shorting plug has been removed, thereby providing an indication that the housing has been removed from the sterile package in preparation for implantation.

38. The method recited in claim 36, wherein the implantable pulse generator is stored in a sterile package, wherein the confirming step comprises the steps of:

connecting a resistive load between the pair of output terminals prior to storing the pulse generator in the sterile package; and determining when the resistive load has been removed, thereby providing an indication that the housing has been removed from the sterile package in preparation for implantation.

39. The method recited in claim 36, wherein the verifying step comprises the steps of:

sensing a temperature; and determining when the temperature is within a predetermined range corresponding to body temperature.

40. The method recited in claim 35, wherein the step of programming the pulse generating means in a storage mode comprises the steps of:

programming a desired number of pacing functions OFF; and waking-up the pulse generating means periodically to detect if the housing has been properly connected to the lead.

41. The method recited in claim 35, wherein the step of programming the pulse generating means in at least one automatic mode further comprises the steps of programming the pulse generating means into an automatic sensitivity mode.

42. The method recited in claim 35, wherein the step of programming the pulse generating means in at least one automatic mode further comprises the step of programming the pulse generating means into an automatic capture mode.

43. The method recited in claim 35, wherein the pulse generating means includes means for operating in a rate responsive mode, the rate responsive mode being defined by a plurality of rate responsive parameters, wherein:

the step of programming the pulse generating means in at least one automatic mode further comprises the step of automatically determining the plurality of rate responsive parameters so that the pulse generating means may operate in the rate-responsive mode.

44. The method recited in claim 35, wherein the step of programming the pulse generator generating means in at least one automatic mode further comprises the step of programming the pulse generating means into an automatic electrode configuration mode.

45. The method recited in claim 35, wherein the pulse generator includes sensing means for sensing cardiac signals, the sensing means having a plurality of sensitivity settings, further comprising the steps of:

programming a sensitivity threshold test to determine an optimum sensitivity setting for the sensing means;

programming a capture threshold test to determine an optimum output pulse value for the pulse generating means;

programming the sensing means to the optimum sensitivity setting; and programming the pulse generating means to the optimum output pulse value.

46. A system for detecting when an implantable stimulation device has been properly connected to an implantable lead in contact with body tissue, the system including pulse generating means having a pair of output terminals, the system comprising:

means for measuring impedance between the pair of output terminals;

means for determining when the impedance is within a predetermined range, thereby providing a first indication that the pulse generating means has been properly connected to an implantable lead in contact with body tissue; and a redundant sensor having means for confirming when the stimulation device has been properly connected to the implantable lead in contact with body tissue.

47. The system recited in claim 46, wherein the predetermined range corresponds to normal cardiac tissue.

48. The system recited in claim 47, wherein the predetermined range comprises 100–2000 ohms.

49. The system recited in claim 46, wherein:

the redundant sensor comprises a shorting plug connected between the output terminals;

the predetermined range corresponds to a short; and the determining means detects the absence or presence of the shorting plug, thereby indicating that the physician has or has not, respectively, prepared the pulse generator for implant.

50. The system recited in claim 46, wherein:

the redundant sensor comprises a resistive load connected between the output terminals;

the predetermined range corresponds to a value of the resistive load; and the determining means detects the absence or presence of the resistive load, thereby indicating that the physician has or has not, respectively, prepared the pulse generator for implant.

51. The system recited in claim 46, wherein the redundant sensor comprises:

means for sensing temperature; and means for determining when the temperature sensing means detects a temperature within a predetermined range corresponding to body temperature, thereby indicating that the stimulation device has been implanted.

* * * * *